United States Patent
Province et al.

(10) Patent No.: US 6,754,525 B1
(45) Date of Patent: Jun. 22, 2004

(54) REDUCTION OF DEFIBRILLATION REQUIREMENTS THROUGH ACTIVE PRE-SHOCK PACING WITH DEPOLARIZATION VERIFICATION

(75) Inventors: Rose Anne Province, San Jose, CA (US); Patrick D. Wolf, Durham, NC (US)

(73) Assignee: Pacesetter, Inc., Sunnyvale, CA (US)

( * ) Notice: Subject to any disclaimer, the term of this patent is extended or adjusted under 35 U.S.C. 154(b) by 197 days.

(21) Appl. No.: 10/033,740

(22) Filed: Dec. 27, 2001

(51) Int. Cl.$^7$ .................................................. A61N 1/362
(52) U.S. Cl. ............................................................ 607/4
(58) Field of Search ........................................ 607/4–28

(56) References Cited

U.S. PATENT DOCUMENTS

| | | | |
|---|---|---|---|
| 6,081,746 A | 6/2000 | Pendekanti et al. |
| 6,085,116 A | 7/2000 | Pendekanti et al. |
| 6,154,672 A | 11/2000 | Pendekanti et al. |
| 6,292,691 B1 | 9/2001 | Pendekanti et al. |

*Primary Examiner*—Scott M. Getzow
(74) *Attorney, Agent, or Firm*—Steven M. Mitchell

(57) ABSTRACT

An implantable cardiac stimulation device is equipped with a sensor to obtain information indicative of tissue depolarization. The device's processor is programmed to analyze the information to determine a suitable pacing pulse regimen and/or to trigger a cardioversion level stimulus.

43 Claims, 8 Drawing Sheets

REDUCTION OF DEFIBRILLATION REQUIREMENTS THROUGH ACTIVE PRE-SHOCK PACING WITH DEPOLARIZATION VERIFICATION

TECHNICAL FIELD

Methods and/or devices described herein generally relate cardiac pacing therapy. More particularly, they concern methods and/or implantable stimulation devices for determining pacing pulses regimens in response to sensed and/or other information, particularly information indicative of tissue depolarization and/or arrhythmia.

BACKGROUND

A goal of cardiac pacing therapy is to "capture" heart tissue, typically through administration of an electrical stimulus, e.g., a pacing pulse. Capture is achieved when an applied stimulus causes "global" depolarization of the heart's myocardial tissue leading to contraction. The stimulation-capture process allows for therapeutic management of various cardiac functions. For example, abnormal heart tissue contractions, known as arrhythmias, which include bradycardia (slow heart rate), tachycardia (fast heart rate), any markedly irregular rhythm, blocks and/or the presence of premature contractions, are manageable through use of stimulation-capture therapies.

Arrhythmias are often problematic and interfere with a heart's normal pumping function. In a normal heart, a pump cycle beings with a stimulus originating at the sinoatrial node, which then travels to intranodal atrial conduction tracts and the Bachmann's bundle and causes the atria to contract and pump blood into the ventricles. The stimulus next travels to the atrioventricular node, the Bundle of His, and the Purkinje system where the stimulus causes simultaneous contraction of the right ventricle, which pumps deoxygenated blood to the lungs through the pulmonary artery, and the left ventricle, which pumps oxygenated blood to the body through the aorta, the body's main artery. In an arrhythmic heart, the stimulation process is corrupt and capable of disabling the heart's pumping action. Pacing therapy seeks to terminate or overcome arrhythmic processes and allow the heart to function normally.

A variety of methods and implantable devices exist for terminating arrhythmia and/or pacing heart contractions. For example, U.S. Pat. Nos. 6,081,764 (Pendekanti, et al.) and 6,085,116 (Pendekanti, et al.) disclose methods and implantable devices for atrial defibrillation and U.S. Pat. No. 6,154,672 (Pendekanti, et al.) discloses methods and implantable devices for ventricle defibrillation. The '764, '116 and '672 patents are, for all purposes, incorporated herein by reference.

According to the '764 and '116 patents, a pacing pulse regimen is used to reduce the shock energy required to terminate atrial fibrillation or to even eliminate the need for a defibrillation shock (a cardioversion level stimulus). In this approach, the pacing pulse regimen constitutes a first treatment tier and the defibrillation shock constitutes a second treatment tier. The first tier pacing pulse regimen consists of a train of pulses delivered to one or more pacing sites in the atrium over a duration of approximately 1 second to 10 seconds. Throughout the duration of the pulse train, the pacing interval (time between successive pulses in the train) at any given pacing site is calculated as a percentage (e.g., preferably 80% to 95%) of the atrial fibrillation cycle length (AFCL), which is the time between successive atrial fibrillations. Thus, given an AFCL value on the order of 100 ms, a two second pulse train will deliver approximately 20 pulses. According to the '764 and '116 patents, the otherwise fixed pulse rate may be incremented after each pulse by a prescribed amount, which is not determined in real time.

These two patents also disclose increasing the pulse interval for verification of capture, or alternatively, decreasing the pulse interval if capture is not verified. However, the '764 and '116 patents do not disclose methods to determine, sense or verify capture. Furthermore, methods to increase or decrease the pulse interval in relation to capture are not disclosed.

The aforementioned '672 patent discloses methods and devices for ventricular pacing therapy for terminating ventricular fibrillation. According to the '672 patent, an equal-interval train of pulses is administered to ventricular tissue with a pulse interval based on the ventricular fibrillation cycle length (VFCL), which is the time between successive ventricular fibrillations. The '672 patent discloses a two tier approach that applies a first tier pacing pulse train to reduce the energy required by a second tier ventricular defibrillation shock. The '672 patent does not disclose sensing or detection of ventricular depolarization in response to pulsing. Instead, only VFCL is detected, which is subsequently used to modify the pacing therapy.

Accordingly, there is a need for pacing therapy that determines pacing pulse regimens and/or whether to administer cardioversion level stimuli on the basis of information indicative of tissue depolarization, in particular, regional or local depolarization.

SUMMARY

An implantable cardiac stimulation device is programmed to administer pacing therapy based, at least in part, on information indicative of tissue depolarization. In essence, information indicative of tissue depolarization may allow one to assess the effectiveness of a stimulation pulse administered to the heart. In one implementation, a pacing pulse is administered to heart tissue. Next, a sensor obtains information indicative of tissue depolarization related to the administered pulse. This pulse-sense cycle is optionally repeated and the information analyzed to determine whether parameters for a subsequent pacing pulse (or pulses) should be altered, or alternatively, whether a cardioversion level stimulus should be delivered.

This approach, as discussed herein, extends beyond that contemplated by traditional pacing therapies in that information indicative of depolarization, in particular regional or local depolarization, is obtained and analyzed in real time, for example, during a pacing pulse regimen. As described herein, regional and local refer to tissue proximate to a stimulus electrode or electrodes. Various methods described herein optionally aim to depolarize tissue in a controllable and coherent manner. Information germane to depolarization is useful to determine and/or modify a pacing pulse regimen in real time, as well as, to determine whether a cardioversion level stimulus should be administered. The methods and devices disclosed herein are further optionally useful in applications that use multiple sense and/or stimulation electrodes in one or more chambers of the heart.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
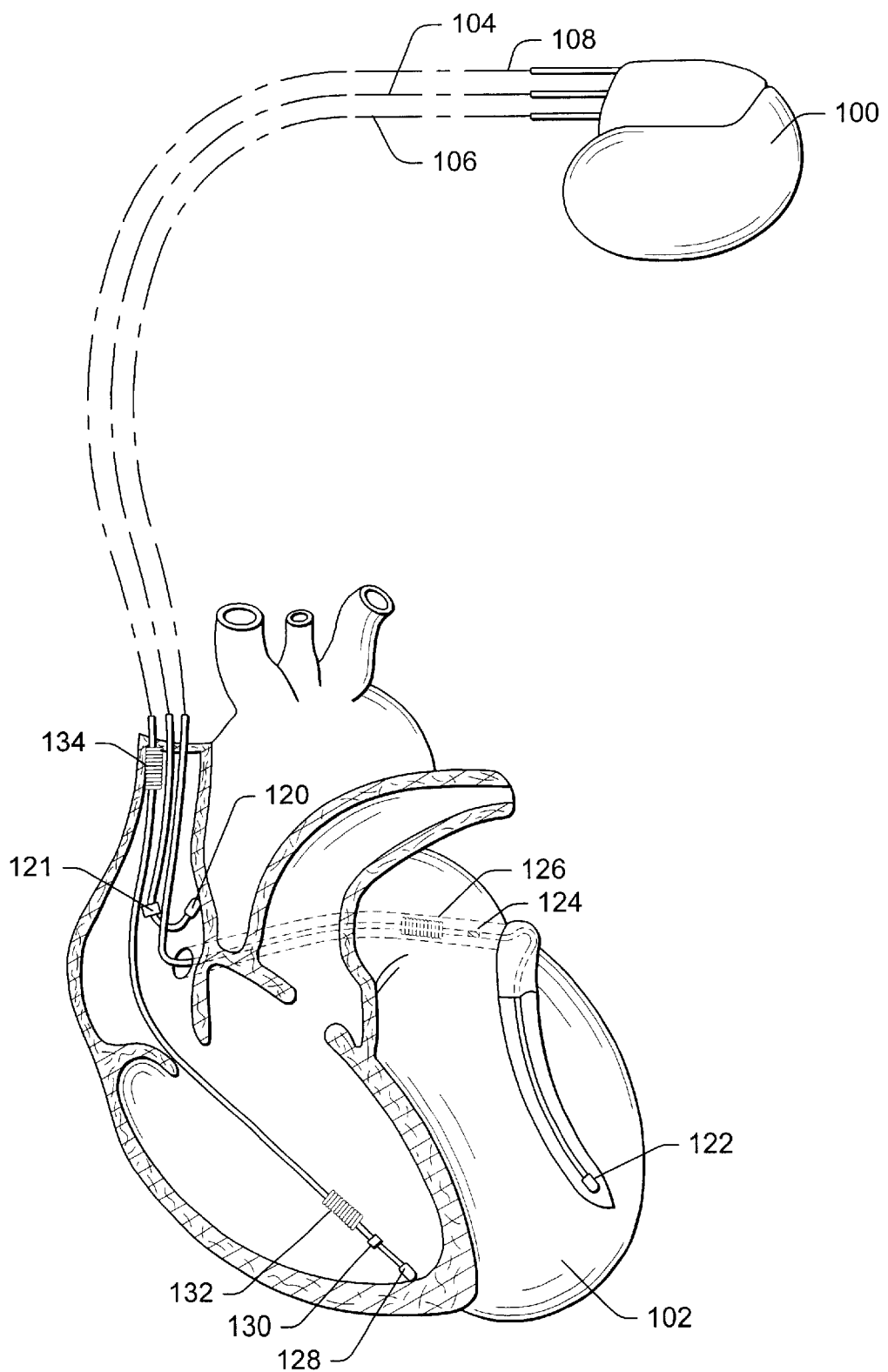
FIG. 1 is a simplified diagram illustrating an exemplary implantable stimulation device in electrical communication with leads implanted into a patient's heart for delivering multi-chamber stimulation and shock therapy.

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

Pacing therapies for treating arrhythmias commonly involve two tiers. For example, a therapy may involve a first tier that administers pacing pulses to precondition heart tissue thus making the tissue more susceptible to administration of a second tier cardioversion level stimulus for terminating arrhythmia. In the first tier, pacing pulses precondition heart tissue through regional (e.g., local) depolarization while, in the second tier, cardioversion level stimulus is directed to a more global depolarization (e.g., capture) that terminates arrhythmia.

In an exemplary process, an implantable device is programmed, or otherwise designed, with a first tier that administers a pacing pulse and then senses for the onset of local depolarization responsive to the pulse. In this exemplary pulse-sense process, depolarization information gathered during sensing is used to determine or modify the administration of a subsequent pacing pulse (or pulses) or to initiate a second tier cardioversion level stimulus. Of course, sensing using the same and/or different sensors may be used to gather information on arrhythmic activity, for example, information concerning an arrhythmia cycle length (ACL). In general, an ACL corresponds to the period between arrhythmic events and, as described below, is optionally useful to initiate and/or modify first tier therapy.

As described herein, various algorithms may be used to analyze information indicative of local depolarization to determine: (i) whether and/or what degree of depolarization has occurred; (ii) how to determine or modify subsequent pacing pulses; and/or (iii) whether a second tier cardioversion level stimulus is required. Of these three groups, algorithms to determine or modify subsequent pacing pulses are of particular interest, especially algorithms that tend to increase the degree of tissue depolarization. Increased first tier tissue depolarization (in response to an applied stimulus) is helpful because the energy needed for second tier arrhythmia termination is typically inversely proportional to the degree of first tier tissue depolarization. In addition, a high degree of first tier tissue depolarization can, in some circumstances, eliminate the need for a second tier cardioversion level stimulus.

Exemplary pulse-sense pacing methods and devices described herein are useful for treating atrial and/or ventricular arrhythmias, especially tachyarrhythmias. The pulse-sense pacing methods are also suitable for use with a variety of sensor and electrode configurations. At a minimum, one sensing and one pacing electrode are required, which optionally operate on the same physical lectrode. If second tier therapy is enabled, then at least one cardioversion level stimulation electrode is needed. A more global approach to sensing is also possible wherein, for example, the case of the therapy device is used as an electrode. Another optional electrode configuration comprises a plurality of electrodes at pacing sites that are controlled by a single sensing site while yet another configuration comprises a plurality of electrodes at sensing sites that are optionally used to control groups of one or more pacing electrodes or pacing sites.

In implementing therapies for the numerous electrode configurations, some which are given above, an implantable device optionally comprises additional hardware and/or software features that allow for independent and/or coordinated pulse and sense operations. For example, if more than one sensing site is used, the therapy optionally operates two independent first tier control processes in parallel. Once depolarization responsive to the pulsing is detected at, for example, all sensing sites, a second tier cardioversion level stimulus is optionally administered within a set time window (e.g., 20% of ACL) after activation occurrences at both sites.

Exemplary Stimulation Device

The techniques described below are intended to be implemented in connection with any stimulation device that is configured or configurable to stimulate or shock a patient's heart.

FIG. 1 shows an exemplary stimulation device 100 in electrical communication with a patient's heart 102 by way of three leads 104, 106, and 108, suitable for delivering multi-chamber stimulation and shock therapy. To sense atrial cardiac signals and to provide right atrial chamber stimulation therapy, stimulation device 100 is coupled to an implantable right atrial lead 104 having at least an atrial tip electrode 120, which typically is implanted in the patient's right atrial appendage. As shown in FIG. 1, the right atrial lead 104 also includes a right atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et. al); and U.S. Pat. No. 5,466,254, "Coronary Sinus Lead with Atrial Sensing Capability" (Helland), which are incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
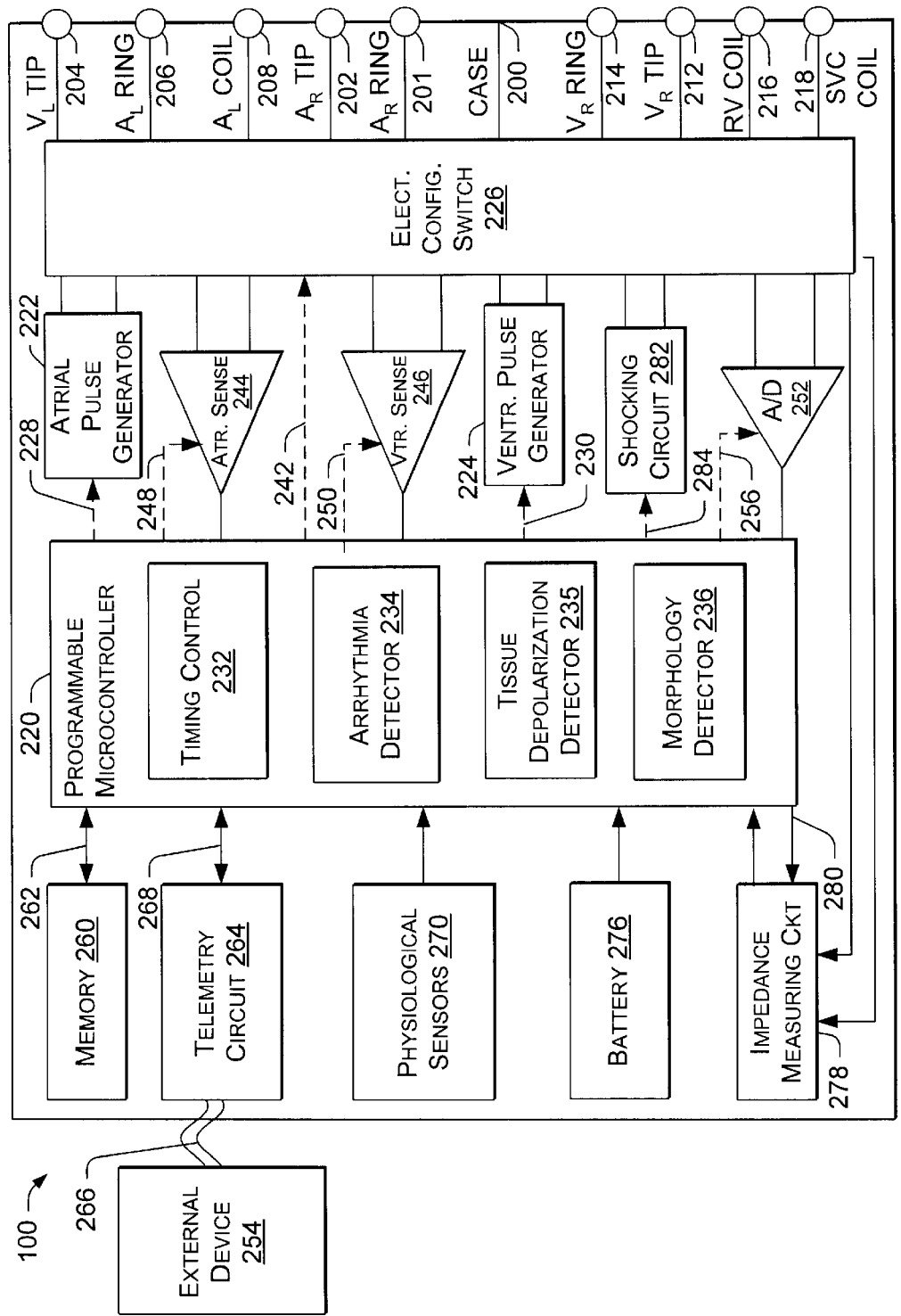
FIG. 2 is a functional block diagram of an exemplary multi-chamber implantable stimulation device illustrating basic elements that are configured to provide cardioversion, defibrillation, and pacing stimulation in four chambers of the heart. The implantable stimulation device is further configured to sense information and administer stimulation pulses responsive to such information.

FIG. 2 shows an exemplary block diagram depicting various components of a simulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

A housing 200 for the stimulation device 100 is often referred to as the "can", "case" or "case electrode", and may be programmably selected to act as the return electrode for all "unipolar" modes. The housing 200 may further be used as a return electrode alone or in combination with one or more of the coil electrodes 126, 132 and 134 for shocking purposes. The housing 200 further includes a connector (not shown) having a plurality of terminals 201, 202, 204, 206, 208, 212, 214, 216, and 218 (shown schematically and, for convenience, the names of the electrodes to which they are connected are shown next to the terminals).

To achieve right atrial sensing and pacing, the connector includes at least a right atrial tip terminal ($A_R$ TIP) 202 adapted for connection to the atrial tip electrode 120. As shown in FIG. 2, the block diagram also includes a right atrial ring terminal ($A_R$ RING) 201 adapted for connection to the atrial ring electrode 121. To achieve left chamber sensing, pacing, and shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

The stimulation device 100 further includes a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. The microcontroller 220 generally includes the ability to process or monitor input signals (data or information) as controlled by a program code stored in a designated block of memory. The type of microcontroller is not critical to the described implementations; hence, any suitable microcontroller 220 may be used that carries out various functions such as those described herein. The use of microprocessorsed-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Sholder) and 4,944,298 (Sholder), all of which are corporated by reference herein. For a more detailed description of the various timing intervals used within the stimulation device and their inter-relationship, see U.S. Pat. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and the ventricular pulse generators 222, 224 may include dedicated, independent pulse generators, multiplexed pulse generators, or shared pulse generators. The pulse generators 222, 224 are controlled by the microcontroller 220 via appropriate control signals 228, 230, respectively, to trigger or inhibit the stimulation pulses.

The microcontroller 220 further includes timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The microcontroller 220 further includes an arrhythmia detector 234 and optionally a morphology detector 236, an orthostatic compensator 238, and a minute ventilation (MV) response module 240. These components can be utilized by the stimulation device 100 for determining desirable times to administer various therapies. The arrhythmia detector 234, together with other components, may optionally ascertain an arrhythmia cycle length. The components 234–240 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, the switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and/or the right ventricular lead 108, through the switch 226 for detecting the presence of cardiac activity in each of the four chambers of the heart. Accordingly, the atrial (ATR. SENSE) and ventricular (VTR. SENSE) sensing circuits 244, 246, respectively, may include dedicated sense amplifiers, multiplexed amplifiers, or shared amplifiers. The switch 226 determines the "sensing polarity" of the cardiac signal by selectively closing the appropriate switches, as is also known in the art. In this way, the clinician may program the sensing polarity independent of the stimulation polarity. The sensing circuits (e.g., sensing circuits 244, 246) are optionally capable of obtaining information indicative of tissue depolarization.

Each sensing circuit (e.g., sensing circuits 244, 246) preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation. For a complete description of a typical sensing circuit, the reader is directed to U.S. Pat. No. 5,573,550, entitled "Implantable Stimulation Device having a Low Noise, Low Power, Precision Amplifier for Amplifying Cardiac Signals" (Zadeh et al.). For a complete description of an automatic gain control system, the reader is directed to U.S. Pat. No. 5,685,315, entitled "Cardiac Arrhythmia Detection System for an Implantable Stimulation Device" (McClure et al.). Accordingly, the '550 and the '315 patents are hereby incorporated herein by reference.

The outputs of the atrial and ventricular sensing circuits 244, 246 are connected to the microcontroller 220, which, in turn, is able to trigger or inhibit the atrial and ventricular pulse generators 222, 224, respectively, in a demand fashion in response to the absence or presence of cardiac activity in the appropriate chambers of the heart. Furthermore, as described herein, the microcontroller 220 is also capable of analyzing information output from the sensing circuits 244, 246 and/or the data acquisition system 252 to determine or detect whether and to what degree tissue depolarization has occurred and to program a pulse, or pulses, in response to such determinations. The sensing circuits 244, 246, in turn, receive control signals over signal lines 248, 250 from the microcontroller 220 for purposes of controlling the gain, threshold, polarization charge removal circuitry (not shown), and the timing of any blocking circuitry (not shown) coupled to the inputs of the sensing circuits 244, 246, as is known in the art.

For arrhythmia detection, the device 100 utilizes the atrial and ventricular sensing circuits 244, 246 to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. Of course, a circuit may accomplish both sensing and detection simultaneously. In addition, such a circuit may also ascertain an event cycle length as well. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by, for example, but not limited to, comparing them to a predefined rate zone limit (i.e., bradycardia, normal, low rate VT, high rate VT, and fibrillation rate zones) and/or various other characteristics (e.g., sudden onset, stability, physiologic sensors, and morphology, etc.). Such classification may aid in the determination of the type of remedial therapy that is needed (e.g., bradycardia pacing, anti-tachycardia pacing, at cardioversion shocks or defibrillation shocks, collectively referred to as "tiered therapy"). An arrhythmia cycle length is optionally ascertained during and/or after arrhythmia sensing and/or detection using the same and/or other components.

Cardiac signals are also applied to inputs of an analog-to-digital (A/D) data acquisition system 252. The data acquisition system 252 is configured to acquire intracardiac electrogram signals, convert the raw analog data into a digital signal, and/or store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

Advantageously, the data acquisition system 252 (or other system or circuitry, e.g., atrial sensing circuitry 244 and ventricular sensing circuitry 246) may be coupled to the microcontroller 220, or other detection circuitry, for analyzing the obtained information to detect an evoked response from the heart 102 in response to an applied stimulus, thereby aiding in detection of local tissue depolarization and/or global tissue depolarization, i.e., "capture." Global tissue depolarization or capture generally corresponds with contraction of cardiac tissue. For example, the microcontroller 220 is capable of analyzing obtained information to detect a depolarization signal during a window following a stimulation pulse, the presence of which typically indicates that some degree of tissue depolarization has occurred. In one implementation, the microcontroller 220 enables depolarization detection by triggering the ventricular pulse generator 224 to generate a stimulation pulse, starting a depolarization detection window using the timing control circuitry 232 within the microcontroller 220, and enabling the data acquisition system 252 via control signal 256 to sample the cardiac signal that falls in the depolarization detection window. The information obtained through the data acquisition system 252 is then analyzed to determine whether and/or to what degree tissue depolarization has occurred. This analysis optionally uses signal amplitude, gradient, integral, etc. to ascertain whether tissue activation has occurred and, if so, to ascertain a corresponding activation time or times. Such results are useful in determining, for example, pacing pulse regimens and/or whether to administer cardioversion level stimuli.

To facilitate detection of tissue depolarization, the microcontroller 220 comprises a dedicated tissue depolarization detector 235, implemented in hardware and/or software. This detector 235 is capable of analyzing information obtained through the sensing circuits 244, 246 and/or the data acquisition system 252. The detector 235 analyzes the sensed information to produce a result, such activation time. Of course, the detector 235 is also capable of noting whether activation has occurred during any given time period. The detector 235 or other microprocessor features can use these results to determine pacing pulse regimens and/or other actions. As described herein, the detector 235 optionally detects local and/or global depolarization.

Depolarization detection, in response to an administered stimulus (optionally during sinus rhythm), may occur on a beat-by-beat basis, a sampled basis, and/or other suitable basis. A depolarization threshold search may optionally be performed once a day during at least an acute phase (e.g., the first 30 days) and less frequently thereafter. A depolarization threshold search typically begins at a desired starting point (either a high energy level or the level at which depolarization is currently occurring) and decreases energy level until depolarization is lost. The value at which depolarization is lost is known as the depolarization threshold. Thereafter, a safety margin is typically added to the depolarization threshold value.

The implementation of depolarization detection circuitry and algorithms are well known. See, for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Mann et al.), all of which are hereby incorporated herein by reference. The type of depolarization detection system used is not critical to the described implementations.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (McClure et al.), which patents are incorporated herein by reference.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 Bornzin et. al), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 optionally monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 $\mu A$), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected. Accordingly, the device 100 preferably employs lithium derivative battery chemistries.

The stimulation device 100 can further include magnet detection circuitry not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. Various exemplary methods of ICD operation are described below. According to various methods, the microcontroller 220 controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are typically applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses. The term "cardioversion level" and/or "cardioversion", as used herein, include shocks having low, moderate and high energy levels, i.e., cardioversion level shocks and defibrillation shocks.

Pulse Determination

In an exemplary process, an implantable device is programmed to administer a pacing pulse and then sense for the onset of tissue depolarization in a region proximate to the pulse administration. This pulse-sense sequence is repeated for a given period of time, referred to herein as the depolarization detection period. According to this exemplary process, sensing depolarization comprises, for example, the use of a sense electrode capable of sensing voltage over time. With this information, the process can determine the voltage gradient, i.e., the change in voltage for a given time period (dV/dt), elicited by the tissue in response to any given pacing pulse and, more importantly, the time of the response. In general, a high magnitude voltage gradient corresponds to a tissue response, or activation, indicative of depolarization. Of course, voltage gradient sensing may be used alone or in conjunction with amplitude sensing to better characterize the tissue response. For example, a voltage response with a high magnitude gradient and a high magnitude amplitude is more indicative of activation than a high magnitude gradient with a low magnitude amplitude.

During a depolarization detection period, once activation is detected, the time of the activation is recorded. This time is then compared to other activation times recorded during the given depolarization detection period, if any. If a given number of the activation times fall within a set limit (e.g., standard deviation limit, etc.) then depolarization is "verified". Depolarization verification is optionally followed by a cardioversion level stimulus (e.g., a stimulus aimed at defibrillating heart tissue). However, if no activation is detected during the depolarization detection period, the number of activations is insufficient, and/or one or more of the activation times fall outside the set limit, then a new depolarization detection period optionally commences, or alternatively, a global timeout is reached and the process is terminated. If a new depolarization detection period commences, then the timing of the pacing pulse is altered, for example, decremented by a set amount or percentage. An exemplary process wherein the pacing pulse is based on an arrhythmia cycle length (ACL) is described below with reference to FIGS. 3–7 and another exemplary process using more than one sensing site is described further below with reference to FIG. 8.

FIGS. 3–8 show exemplary processes for sensing information and for administering an appropriate pacing therapy based on sensed information and/or other information. Various methods described herein, and equivalents thereof, can be implemented in connection with any suitably configured stimulation device. One specific and non-limiting example of a stimulation device was described above with respect to FIGS. 1 and 2.

In the flow diagrams of FIGS. 3–8, various algorithmic acts are summarized in individual "blocks".Such blocks describe specific actions or decisions that are made or carried out as the process proceeds. Where a microcontroller (or equivalent) is employed, the flow charts presented herein provide a basis for a "control program" or software/firmware that may be used by such a microcontroller (or equivalent) to effectuate the desired control of the stimulation device. As such, the processes are implemented as machine-readable instructions stored in memory that, when executed by a processor, perform the various acts illustrated as blocks.

Those skilled in the art may readily write such a control program based on the flow charts and other descriptions presented herein. It is to be understood and appreciated that the inventive subject matter described herein includes not only stimulation devices when programmed to perform the acts described below, but the software that is configured to program the microcontrollers and, additionally, any and all computer-readable media on which such software might be embodied. Examples of such computer-readable media include, without limitation, floppy disks, hard disks, CDs, RAM, ROM, flash memory and the like.

Exemplary processes comprising, for example, an initialization and wait period, a pulse-sense loop, and/or a depolarization verified procedure are shown with reference to FIGS. 3–7. In general, arrhythmia sensing, detection and/or ascertaining occur prior to such exemplary processes. According to various exemplary processes, a device ascertains an arrhythmia cycle length prior to administration of a therapy aimed at terminating an arrhythmia.

Figure 3:
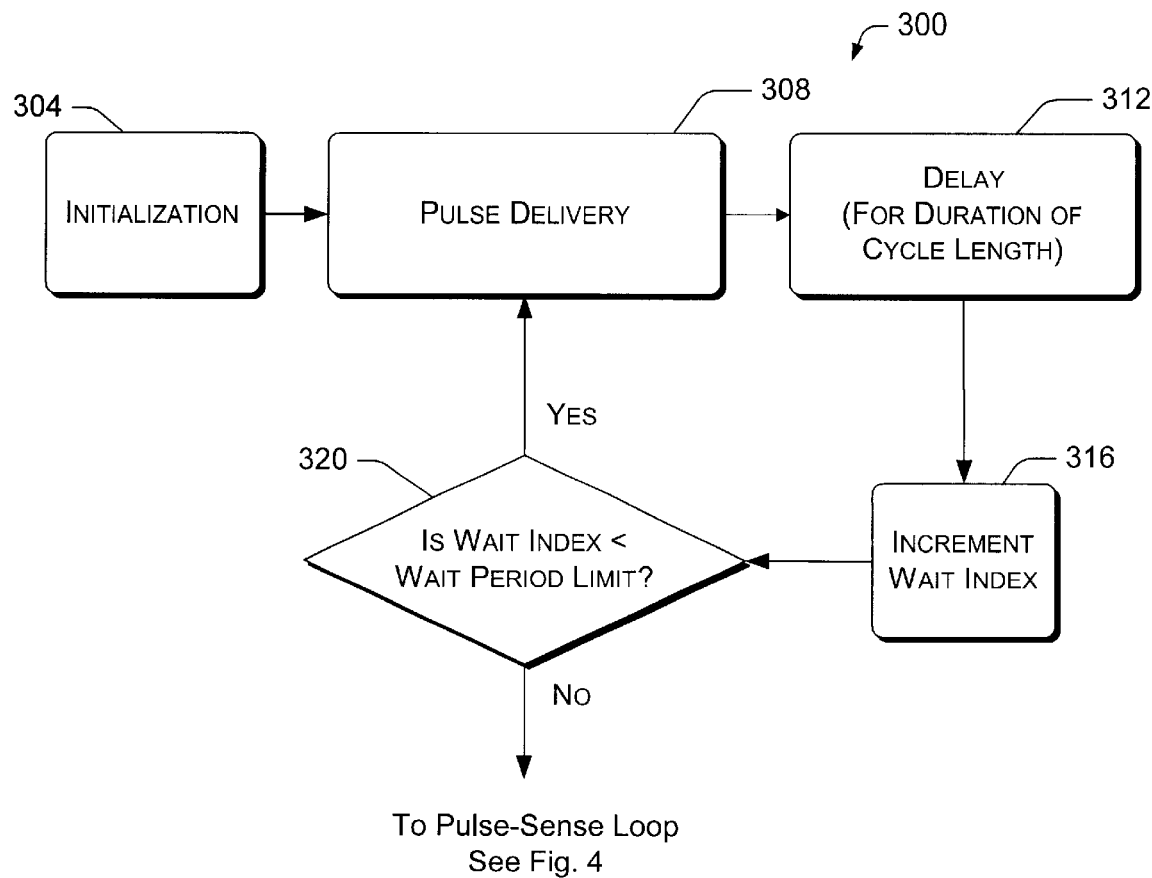
FIG. 3 is a functional block diagram of an exemplary initialization and wait process for use in a procedure that administers a pulse and senses a tissue response to the pulse.

Referring to FIG. 3, in an initialization and wait period procedure 300, an initialization block 304 initializes various process parameters. For example, the initialization block 304 uses the arrhythmia cycle length (ACL), as sensed, detected and/or otherwise ascertained, to determine and initialize the pacing cycle length (PCL). The initialization block 304 optionally calculates the PCL as a percentage of an ascertained ACL, e.g., 110% of the ACL. Typically, a default percentage value that is greater than 100% helps to ensure that the timing of the initial pacing pulse is not too early. In general, a window for effective cardiac tissue depolarization typically exists between approximately 90% and approximately 110% of the ACL; however, other values may also prove useful. In addition, the initialization block 304 sets a loop counter index to zero and the maximum number of loop iterations for the depolarization detection period (e.g., approximately 10 iterations). Other values, e.g., limits, etc., may also be set by the initialization block 304.

After the initialization block 304, a pulse delivery block 308 delivers a pacing pulse. Next, a delay block 312 causes the process to experience a delay that equals the cycle length. After the delay block 312, a wait index increment block 316 increments the wait index, which was initially set by the initialization block 304. The index typically corresponds to the number of pulse that have been delivered by the pulse delivery block 308. An index check block 320 then checks the index to see if the index is within a wait period limit, for example, set by the initialization block 304. If the index is less than the limit, then the pulse delivery block 308 delivers another pulse and the process continues until the limit is reached. Note that blocks 308, 312, 316 and 320 form a wait loop. Such a wait loop may allow for stabilization of local tissue responding to pacing. In some instances, a coherent response may occur only after a series of pulses, e.g., approximately 20 pulses. Once the index exceeds the limit, see index check block 320, then a pulse-sense loop (see, e.g., pulse-sense loops 400, 600 of FIGS. 4 and 6, respectively) commences.

Figure 4:
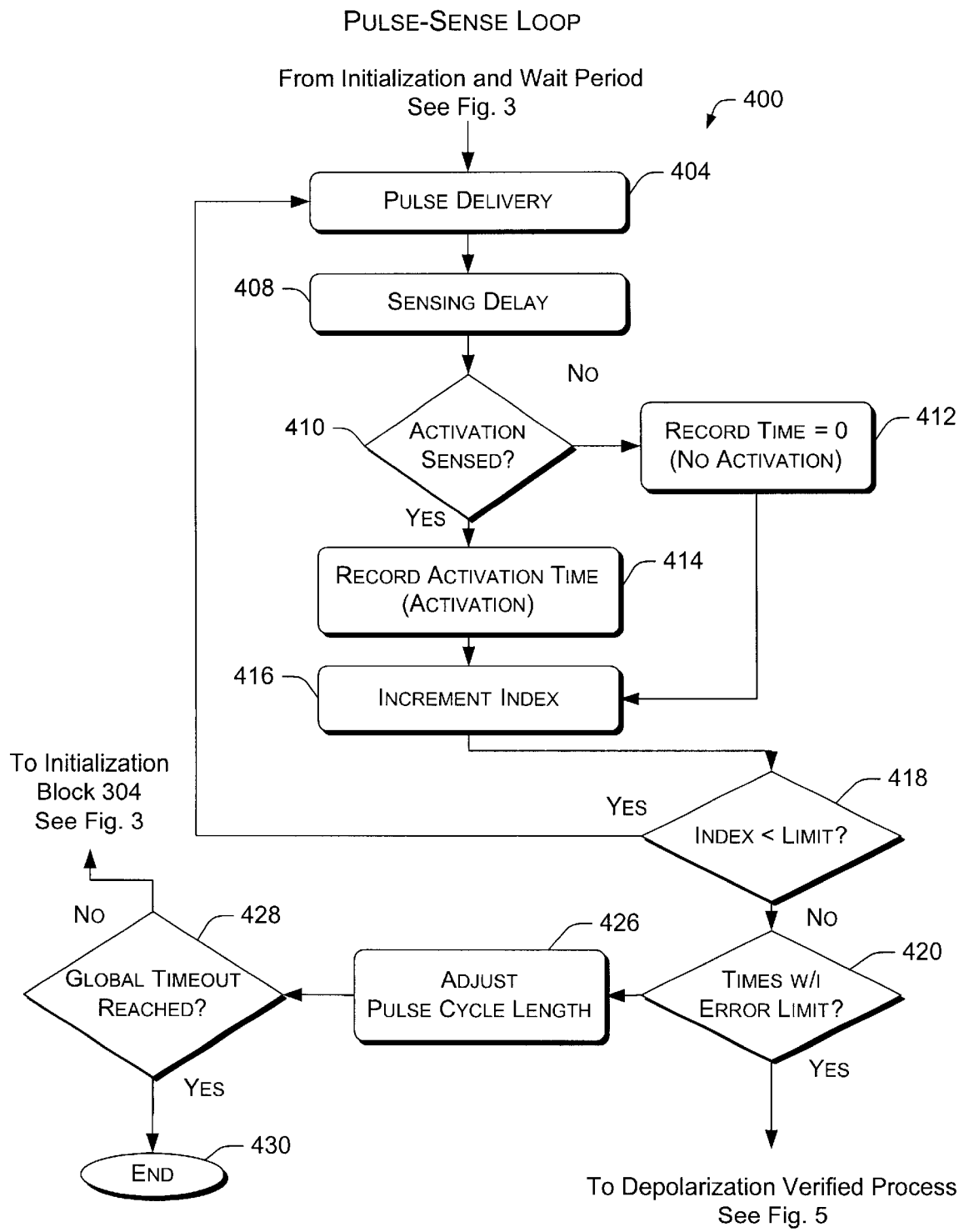
FIG. 4 is a functional block diagram of an exemplary pulse-sense loop process for administering a pulse and sensing tissue response to the pulse.

FIG. 4 shows a pulse-sense loop that commences with a pulse delivery block 404 that delivers a pulse. Next, a sensing delay block 408 causes a delay prior to sensing wherein the delay approximates a sensing refractory period (e.g., approximately 20 ms). This delay optionally allows for stabilization of a sensing amplifier and may correspond to a period during which all sensed information is ignored.

After the sensing wait period, an activation sensing block 410 senses information indicative of tissue depolarization. The sensing block 410 causes the device to sense activations based on an amplitude limit and/or a gradient limit, which are set, for example, by the initialization block 304. The sensing block 410 also performs a logical operation to ascertain if activation has been detected. If activation is not detected, then a recording block 412 records zero as the activation time. However, if activation is detected, then a recording block 414 records the time of the detected activation relative to the pacing pulse. In the case that multiple activations are detected, then the activation time corresponding to the activation with the highest amplitude is recorded.

After recording (e.g., 412 or 414), a pulse-sense loop increment index block 416 increments the pulse-sense loop index. Next, a check block 418 checks if the index is within a pulse-sense loop limit, which is optionally set by the initialization block 304. If the index is less than the limit, then the pulse-sense process 400 returns to the pulse delivery block 404. The process 400 continues until the pulse-sense loop index limit is reached.

Once the limit is reached, an activation time comparison block 420 compares recorded activation times to determine whether the recorded activation times, for a set number of pulse-sense loop iterations (which essentially constitutes a depolarization detection period), are within a set limit, for example, within +/−10 ms of each other. If the activations times fall within this set limit, then depolarization is verified and the process 400 terminates and a depolarization verified process commences (see FIG. 5). However, if any of the activation times fall outside the set limit, then a PCL adjustment block 426 adjusts the timing of the pulse-sense loop pulse.

In this exemplary process 400, the PCL adjustment block 426 decreases the PCL by a set amount (e.g., 2 ms) or percentage (e.g., 2%). If the PCL is less than a set limit (e.g., 90% of the ACL), then the PCL adjustment block 426 resets the PCL to, for example, 110% of the ACL. After the PCL adjustment block 426, a global timeout check block 428 performs a global timeout check. According to the operation of the global timeout check block 428, if depolarization is not verified after a set number of depolarization detection periods or after a set period of time (e.g., 10 min.), then the pulse-sense loop 400 terminates via a global termination block 430.

Figure 5:
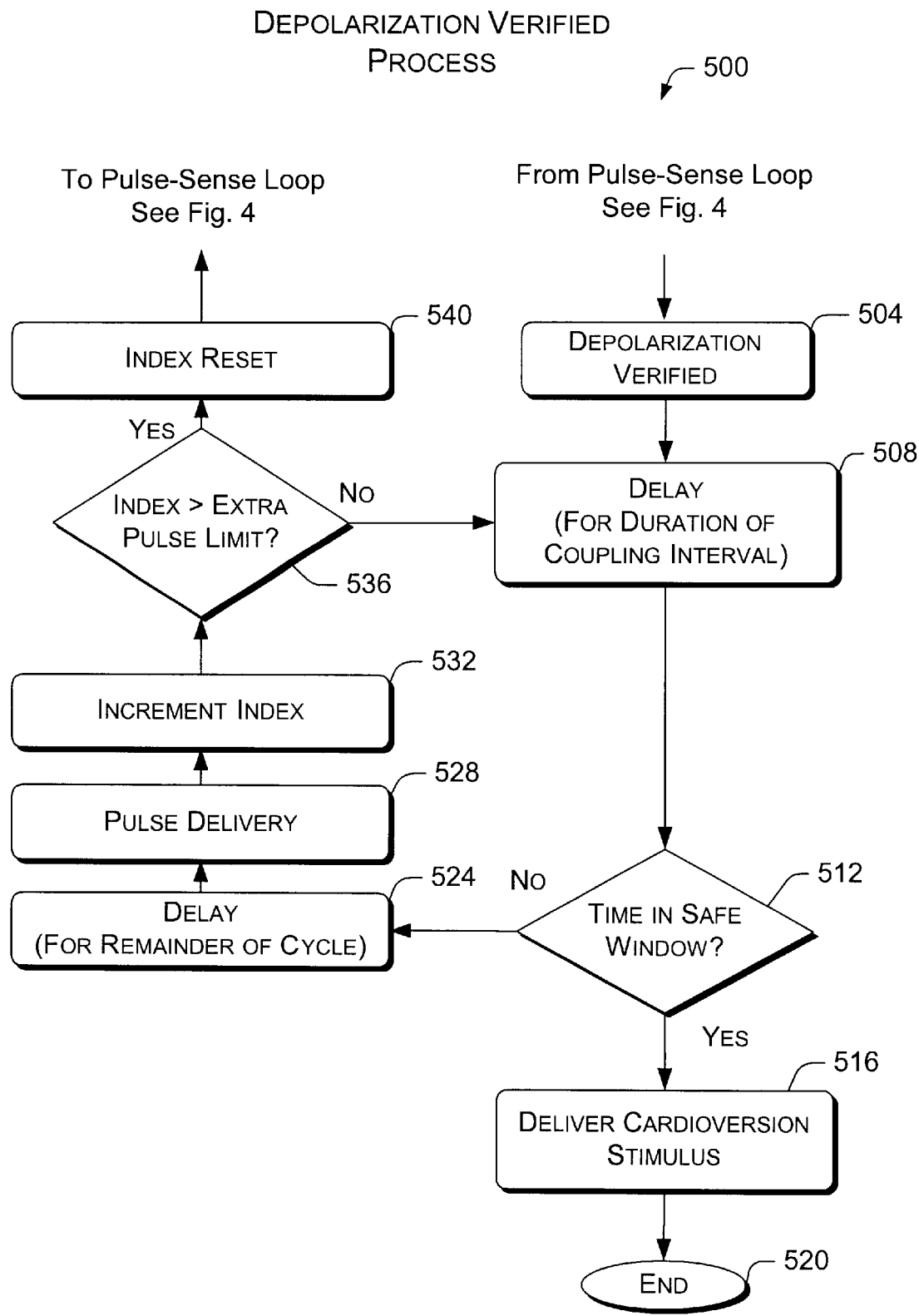
FIG. 5 is a functional block diagram of an exemplary depolarization verified process for administering a pulse and/or a cardioversion level stimulus to a patient.

FIG. 5 shows a flow chart for a depolarization verified process 500. A depolarization verified block 504 verifies depolarization and optionally determines whether the arrhythmia has been terminated by the pulse-sense loop 400. If the arrhythmia has been terminated, then the process 500 terminates. Next, a delay block 508 delays the process for the duration of the coupling interval, which may comprise a fraction of the cycle length, e.g., approximately 90% of the cycle length. After the delay, a check block 512 determines whether the time is within a safe window. The safe window is optionally defined relative to the timing of activation in the ventricle, which may include the R wave and a time window following the R wave before the beginning of the ventricular vulnerable period. If the time is within the safe window, then a cardioversion level stimulus block 516 delivers a cardioversion level stimulus in an effort to terminate the arrhythmia. A termination block 520 terminates the process 500 thereafter.

If, however, the delay block 512 determines that the time is outside of the safe window, then another delay block 524 delays for the remainder of the cycle length. Next, another pulse delivery block 528 delivers a pulse. An index increment block 532 increments yet another index, which is checked by a check block 536 to determine whether the index has exceeded an extra pulse limit. If the index is less than the limit, then the process 500 returns to the delay block 508. In the case that the index is greater than the limit, an index reset block 540 resets the index to zero and the pulse-sense loop procedure 400 is optionally repeated.

The exemplary procedure comprising the initialization and wait period shown in FIG. 3, the pulse-sense loop shown in FIG. 4, and the depolarization verified procedure shown is FIG. 5 is useful for treating arrhythmia. For example, an implantable stimulation device detects atrial fibrillation in a patient. An endocardial catheter placed in the patient's right atrium then senses local atrial activations. During initialization process, a median cycle length and an activation amplitude are determined from data received through a sense electrode. On the basis of this cycle length, a pacing cycle length and thresholds for activation are determined.

Next, pacing of the patient's heart tissue commences using the pacing cycle length. The pacing initially consists of a series of pulses, delivered during a "wait" period, which allows heart tissue responding to the pulses to stabilize. Following this wait period, a pulse-sense loop commences in an effort to pace the heart tissue. As described above, the pacing interval in the pulse-sense loop varies in response to activation sensing. Finally, if activation sensing records a series of activation times that meet certain criteria, then depolarization is verified for the patient.

Once depolarization is verified, a delay occurs that, for example, equals the coupling interval between a cardioversion level shock and the most recent pacing pulse (e.g., approximately 95% of the current pacing cycle length). Next, the timing of the last ventricular depolarization wave is checked against a safe window time reference. If the time is within the safe window, then the implantable stimulation device administers a cardioversion level shock to the patient. The safe window normally comprises a time period that avoids the T wave. For example, the safe window may lie in a time frame between an R wave and 200 ms thereafter or in a time frame that commences more than 600 ms after an R wave. If however, the time falls outside of the safe window, then a depolarization verified procedure optionally delivers a pacing pulse instead of a cardioversion level stimulus. If a certain number of pacing pulses are delivered before a cardioversion stimulus, or before termination of the arrhythmia, then the process either terminates or a pulse-sense loop recommences.

Figure 6:
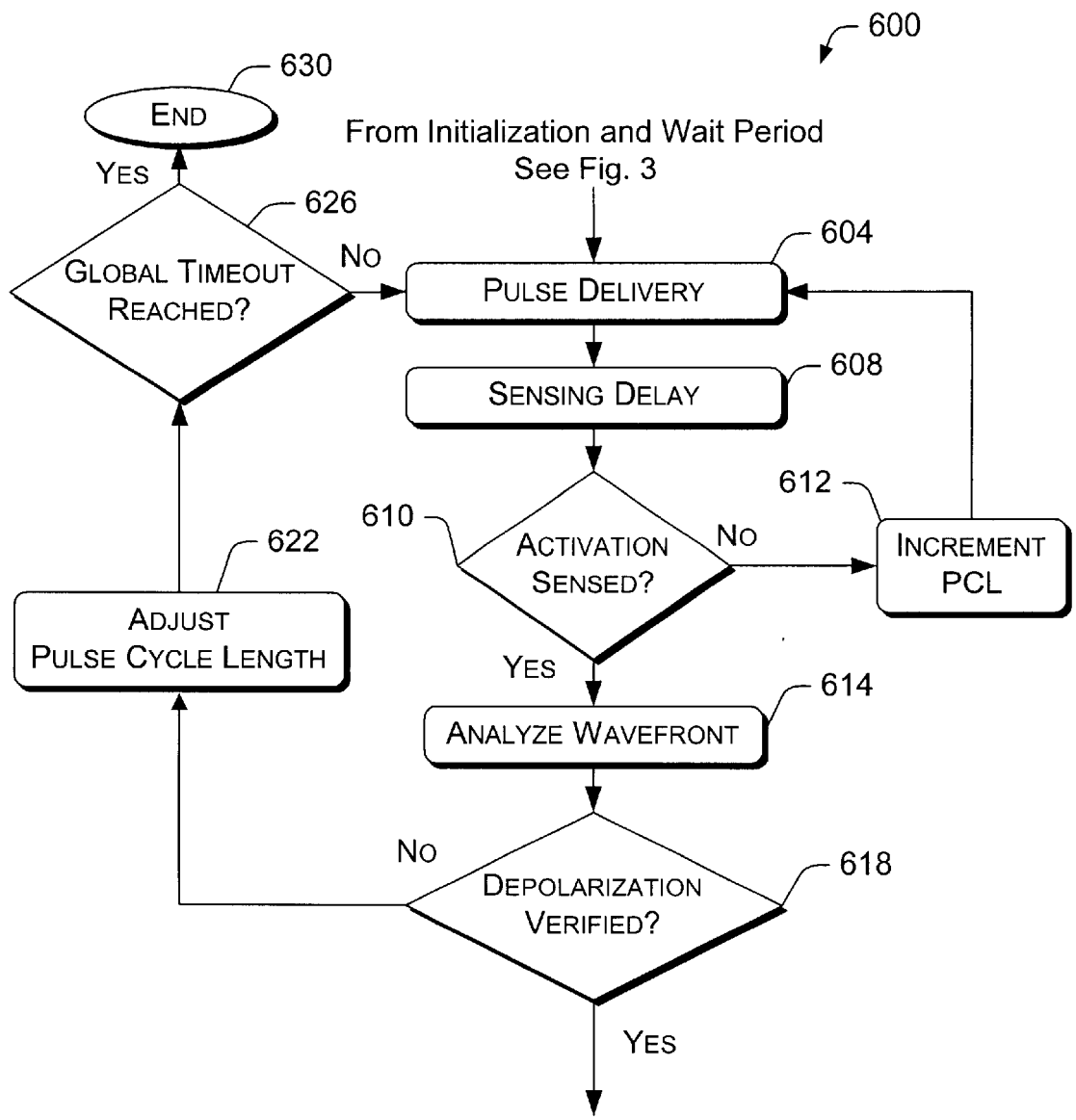
FIG. 6 is a functional block diagram of an exemplary pulse-sense loop process for administering a pulse and sensing tissue response to the pulse.

Referring to FIG. 6, an alternative pulse-sense loop 600 is shown. The pulse-sense loop commences with a pulse delivery block 604 that delivers a pulse. Next, a sensing delay block 608 causes a delay prior to sensing wherein the delay approximates a sensing refractory period (e.g., approximately 20 ms). This delay optionally allows for stabilization of a sensing amplifier and may correspond to a period during which all sensed information is ignored.

After the sensing wait period, an activation sensing block 610 senses information indicative of tissue depolarization. The sensing block 610 causes the device to sense activations based on an amplitude limit and/or a gradient limit, which are set, for example, by the initialization block 304. The sensing block 610 also performs a logical operation to ascertain if activation has been detected.

If the sensing block 610 detects activation, then a wavefront analysis block 614 analyzes the activation signal wavefront; however, if the sensing block 610 does not detect activation, then a pacing cycle length (PCL) increment block 612 increments the PCL and returns to the pulse delivery block 604 and the pulse-sense loop continues. In the case of activation, a depolarization verification block 618 uses information from the analysis block 614 to verify the existence and/or extent of depolarization. If the verification block 618 verifies depolarization, then the method enters a depolarization verified process, such as that described above with reference to FIG. 5. If the verification block 618 does not verify depolarization, then a PCL adjustment block 622 adjusts the timing of the pulse-sense loop pulse. A timeout check block 626 follows wherein a timeout terminates the process at a termination block 630. In the absence of a timeout, the pulse-sense loop continues at the pulse delivery block 604.

Figure 7:
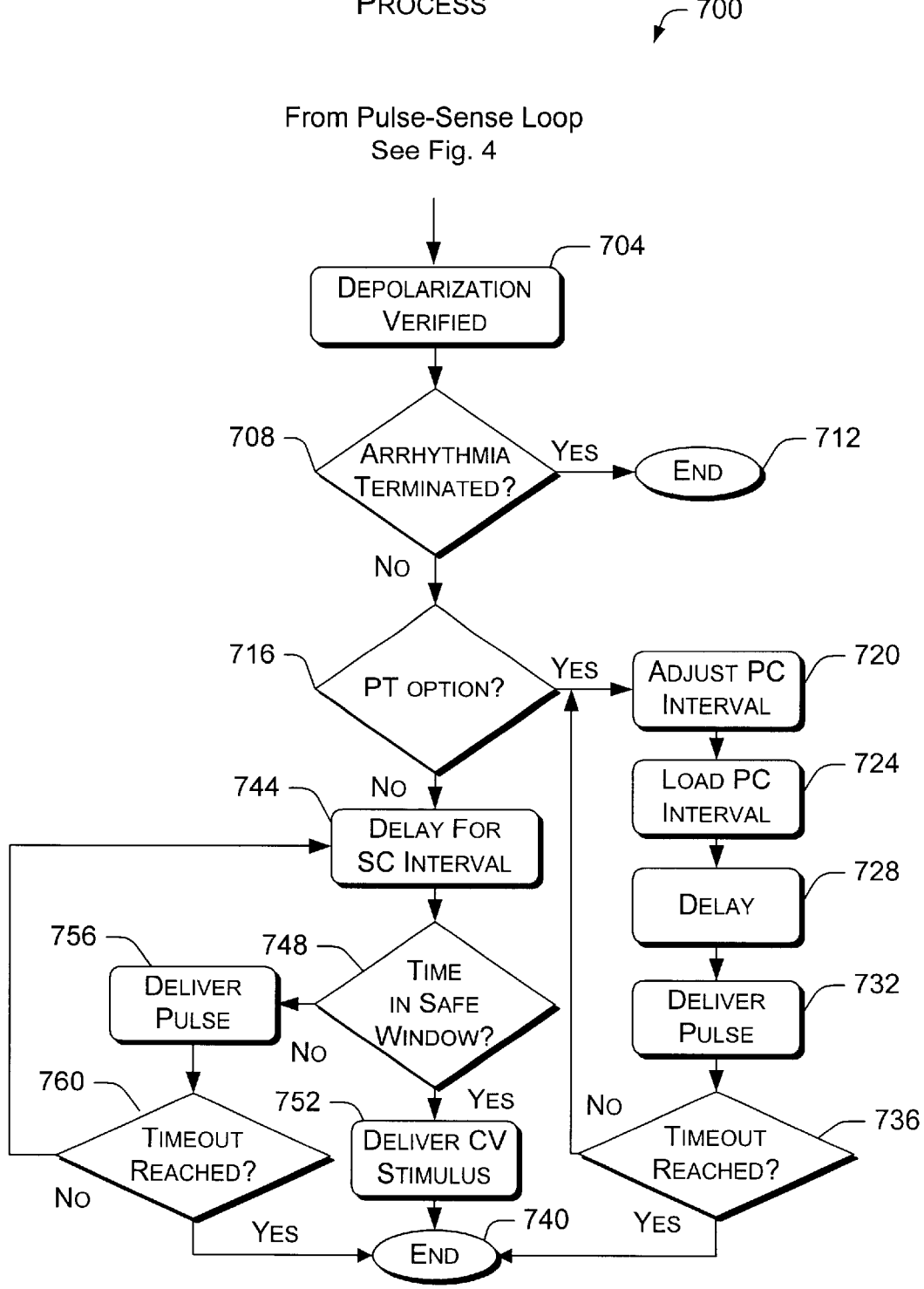
FIG. 7 is a functional block diagram of an exemplary depolarization verified process for administering a pulse and/or a cardioversion level stimulus to a patient.

Referring to FIG. 7, an alternative depolarization verified process 700 is shown. A depolarization verified block 704 verifies depolarization. Next, an arrhythmia check block 708 determines whether the arrhythmia has been terminated by the pulse-sense loop (e.g., the pulse-sense loop of FIG. 4 or FIG. 6). If the arrhythmia has been terminated, then the process 700 terminates at a termination block 712. If an arrhythmia persists, a pacing termination (PT) check block 716 checks whether a PT option is enabled. If this option is not enabled, a delay block 744 delays the process 700 for the duration of the shock coupling interval. Next, a time check block 748 checks the time to determine whether it falls within a safe window. If the time falls within a safe window, a delivery block 752 delivers a cardioversion level stimulus and terminates at a termination block 740. If the time falls outside of a safe window, then a delivery block 756 delivers a pacing pulse. A timeout check block 760 follows wherein a timeout terminates the process 700 at the termination block 740. In the absence of a timeout, the process 700 continues to the delay block 744.

If the PT option is enabled, the process 700 enters a different loop commencing with a pace coupling (PC) interval adjustment block 720. A load block 724 loads the adjusted PC interval into a timer. Subsequently, a delay block 732 waits for a timeout event or a sensed activation event. Following the occurrence of either event, a delivery block 732 delivers a pacing pulse. After delivery of a pacing pulse, a timeout check block 736 determines whether a timeout has occurred, which, terminates the process 700 at the termination block 740. In the absence of a timeout, the process continues at the PC interval adjustment block 720.

Figure 8:
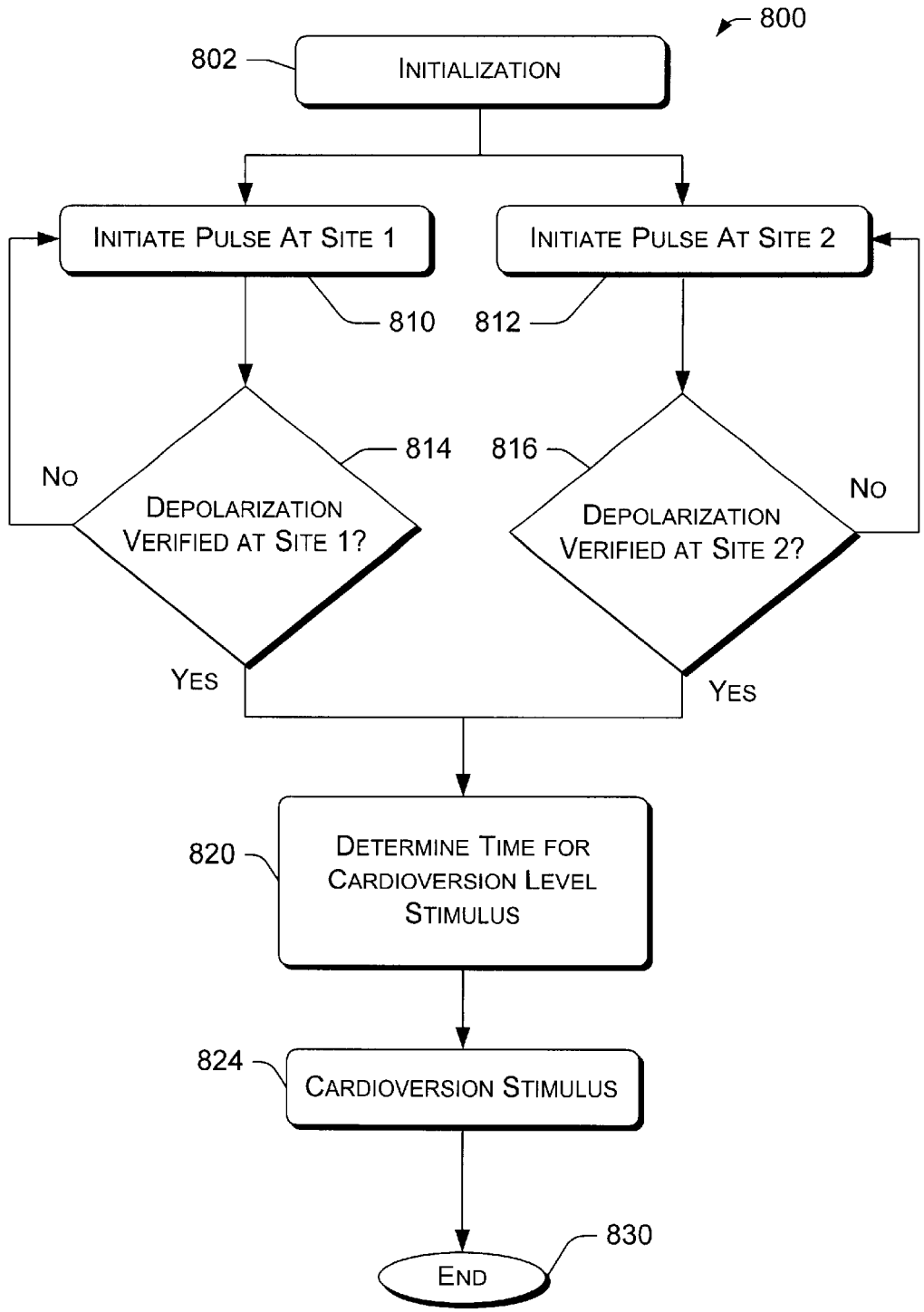
FIG. 8 is a functional block diagram of an exemplary process that uses more than one pulsing and sensing site.

Referring to FIG. 8, an exemplary process 800 is shown wherein more than one sensing site is used. According to this process, two initiation blocks 810 and 812 initiate various parameters and pulses at two different sites. Following the initiation blocks 810 and 812, two depolarization verification blocks 814 and 816 determine whether depolarization has been verified at either site. If depolarization is verified at both sites within a given period of time, information regarding depolarization is output to a subsequent block 820 to determine an appropriate delivery time for a cardioversion level stimulus. Next, a cardioversion level stimulus delivery block 820 delivers a stimulus and a termination block 830 terminates the process 800.

While the exemplary process 800 shown in FIG. 8 is directed to only two sites, other implementations of the methods and devices disclosed herein are applicable to any practical number of sites. In addition, an implementation using multiple sensing sites for obtaining information indicative of tissue depolarization and a fewer number of pulsing sites, or even a single pulsing site, is within the scope of the present invention.

Conclusion

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

What is claimed is:

1. A method for operating an implantable stimulation device, comprising:
   ascertaining an arrhythmia cycle length;
   applying a cardiac stimulation pulse to a site in a patient's heart;
   obtaining information indicative of tissue depolarization proximate to the site and in response to the pulse;
   analyzing the information; and
   determining a pacing pulse regimen based at least in part on the analyzing and at least in part on the arrhythmia cycle length.

2. The method of claim 1, wherein the obtaining comprises receiving sensor data from at least one sensor positioned in the heart.

3. The method of claim 1, wherein the analyzing comprises analyzing the information for an activation time or lack thereof.

4. The method of claim 1, further comprising administering pacing therapy according to the pacing pulse regimen.

5. The method of claim 1, further comprising triggering a cardioversion level stimulus.

6. The method of claim 5, wherein the triggering occurs if the determining terminates the pacing pulse regimen.

7. One or more computer-readable media having computer-readable instructions thereon which, when executed by a programmable stimulation device, cause the stimulation device to execute the method of claim 1.

8. A method for operating an implantable stimulation device, comprising:
- applying a cardiac stimulation pulse to a site in a patient's heart;
- obtaining information indicative of tissue depolarization proximate to the site and a response to the pulse;
- analyzing the information for a result, the result comprising a tissue activation time or lack thereof;
- recording the result;
- repeating the obtaining, the analyzing, and the recording; and
- determining a pacing pulse regimen based, at least in part, on at last one result.

9. The method of claim 8, wherein the determining comprises comparing at least two results.

10. The method of claim 8, wherein the determining comprises comparing results to a depolarization verification error limit.

11. The method of claim 10, wherein the depolarization verification error limit comprises at least one time bound.

12. The method of claim 10, wherein the determining terminates the pacing pulse regimen if the results are within the depolarization verification error limit.

13. The method of claim 10, wherein the pacing pulse regimen comprises a pacing cycle length and the determining decreases the pacing cycle length if any of the results are outside of the error limit.

14. The method of claim 8, further comprising triggering a cardioversion level stimulus.

15. The method of claim 14, wherein the triggering occurs if the determining terminates the pacing pulse regimen.

16. The method of claim 8, further comprising detecting an arrhythmia.

17. The method of claim 16, further comprising ascertaining an arrhythmia cycle length.

18. The method of claim 17, wherein the determining determines the pacing pulse regimen based, at least in part, on the arrhythmia cycle length.

19. The method of claim 18, wherein the recording comprises comparing the result to at least one previous result.

20. One or more computer-readable media having computer-readable instructions thereon which, when executed by a programmable stimulation device, cause the stimulation device to execute the method of claim 8.

21. A method for operating an implantable stimulation device, comprising:
- applying a cardiac stimulation pulse to a site in a patient's heart;
- obtaining information indicative of tissue depolarization proximate to the site and in response to the pulse;
- analyzing the information; and
- determining a pacing pulse regimen for at least two pacing sites in the heart based, at least in part, on the analyzing.

22. The method of claim 21, wherein the obtaining comprises receiving sensor data from at least two sensors positioned in the heart.

23. The method of claim 21, further comprising administering at least one pacing pulse regimen to at least two pacing sites in the heart.

24. One or more computer-readable media having computer-readable instructions thereon which, when executed by a programmable stimulation device, cause the stimulation device to execute the method of claim 21.

25. A method for operating an implantable stimulation device, comprising:
- ascertaining an arrhythmia cycle length;
- sensing information indicative of tissue depolarization responsive to one or more pacing pulses using at least one sensor;
- determining a pacing pulse regimen, based at least in part on the information and at least in part on the arrhythmia cycle length, using a microcontroller; and
- administering the pacing pulse regimen using at least one pacing electrode.

26. The method of claim 25, further comprising analyzing the information for a result, the result comprising a tissue activation time or lack thereof.

27. The method of claim 26, wherein the determining determines the pacing pulse regimen based, at least in part, on the result.

28. The method of claim 25, wherein at least one of the sensor electrodes is also a pacing electrode.

29. One or more computer-readable media having computer-readable instructions thereon which, when executed by a programmable stimulation device, cause the stimulation device to execute the method of claim 25.

30. A cardiac stimulation device comprising:
- a sensor to obtain information indicative of tissue depolarization following delivery of and in response to a pacing pulse;
- a processor operably coupled to the sensor, the processor being configured to determine an arrhythmia cycle length and a pacing pulse regimen based on the information; and
- a pacing generator configured to administer the pacing pulse regimen as directed by the processor.

31. The cardiac stimulation device of claim 30, wherein the information comprises voltage data with respect to time.

32. The cardiac stimulation device of claim 30, wherein the processor analyzes the information for a result, the result comprising a tissue activation time or lack thereof.

33. The cardiac stimulation device of claim 30, wherein the pacing pulse regimen comprises a pacing pulse cycle and the processor determines whether to increase or decrease the pacing pulse cycle.

34. The cardiac stimulation device of claim 33, wherein the processor determines whether to decrease the pacing pulse cycle based, at least in part, on the information.

35. The cardiac stimulation device of claim 30, wherein the pacing generator is further configured to deliver a cardioversion level stimulus.

36. The cardiac stimulation device of claim 35, wherein the processor determines whether to deliver a cardioversion level stimulus based, at least in part, on the information.

37. A cardiac stimulation device comprising:
- at least one sensor to obtain information indicative of tissue depolarization following delivery of and in response to a pacing pulse;
- a processor operably coupled to the sensor, the processor being configured to analyze the information for a result, the result comprising a tissue activation time or lack thereof, and to determine a pacing pulse regimen based, at least in part, on the result; and
- a pacing generator configured to administer a pacing pulse regimen as directed by the processor.

38. The cardiac stimulation device of claim 37, wherein the pacing generator is further configured to deliver a cardioversion level stimulus.

39. The cardiac stimulation device of claim 38, wherein the processor determines whether to deliver a cardioversion level stimulus based, at least in part, on the information.

40. An implantable cardiac rhythm management device, comprising:

sensing means for obtaining information indicative of tissue depolarization following delivery of and in response to a pacing pulse;

processing means for analyzing the information for a result, the result comprising a tissue activation time or lack thereof;

determination means for determining a pacing pulse regimen based, at least in past, on the result; and therapy administration means, responsive to the determination means, for administering a pacing pulse regimen.

41. The device of claim 40, wherein therapy administration means further comprises cardioversion level stimulus administration means.

42. The device of claim 40 further comprising ascertaining means for ascertaining an arrhythmia cycle length.

43. A method of operating an implantable stimulation device, comprising:

ascertaining an atrial arrhythmia cycle length;

applying a sequence of atrial pacing pulses having a rate as a function of the atrial arrhythmia cycle length;

detecting capture or non-capture for at least some of the pacing pulses;

analyzing the results of the detecting step and adjusting the pacing pulse rate of a subsequent sequence of atrial pacing pulses as a function of the analysis.

* * * * *